US012697234B2

(12) United States Patent
Sanders et al.

(10) Patent No.: US 12,697,234 B2
(45) Date of Patent: Aug. 4, 2026

(54) PROSTHETIC SOCKET RELEASE/RELOCK SYSTEM

(71) Applicant: University of Washington, Seattle, WA (US)

(72) Inventors: Joan E. Sanders, Seatlle, WA (US); Joseph L. Garbini, Seattle, WA (US); Clement Gurrey, Seattle, WA (US); Katheryn J. Allyn, Seattle, WA (US); Jake McLean, Seattle, WA (US); Brian Larsen, Seattle, WA (US)

(73) Assignee: University of Washington, Seattle, WA (US)

( * ) Notice: Subject to any disclaimer, the term of this patent is extended or adjusted under 35 U.S.C. 154(b) by 710 days.

(21) Appl. No.: 18/178,138

(22) Filed: Mar. 3, 2023

(65) Prior Publication Data

US 2023/0277341 A1 Sep. 7, 2023

Related U.S. Application Data

(60) Provisional application No. 63/316,309, filed on Mar. 3, 2022.

(51) Int. Cl.
*A61F 2/80* (2006.01)
*A43C 11/16* (2006.01)

(52) U.S. Cl.
CPC .............. *A61F 2/80* (2013.01); *A43C 11/165* (2013.01); *A61F 2002/802* (2013.01)

(58) Field of Classification Search
CPC ..... A61F 2/80; A61F 2002/7831; A43B 7/147
See application file for complete search history.

(56) References Cited

U.S. PATENT DOCUMENTS

| | | | |
|---|---|---|---|
| 6,267,787 | B1 | 7/2001 | Capper |
| 7,217,060 | B2 | 5/2007 | Ingimarsson |
| 7,288,117 | B2 | 10/2007 | Benson |

(Continued)

OTHER PUBLICATIONS

Gardner, David W. et. al, Monitoring Prosthesis User Activity and Doffing Using an Activity Monitor and Proximity Sensors. Journal of Prosthetics and Orthotics 28(2):p. 68-77, Apr. 2016. (Year: 2016).*

(Continued)

*Primary Examiner* — Katrina M Stransky
*Assistant Examiner* — Lukas Milo Lehman
(74) *Attorney, Agent, or Firm* — McDonnell Boehnen Hulbert & Berghoff LLP

(57) ABSTRACT

A device configured to be positioned within a prosthetic socket includes a tether, a spool, a motor, a coupling mechanism, a release actuator, and a tightening actuator. A first end of the tether is configured to be coupled to a prosthetic liner, and a second end of the tether is coupled to the spool. The spool is fixed with respect to the prosthetic socket. The coupling mechanism transitions from a first position in which the spool is restricted to rotate in a first direction to a second position in which the spool is not restricted. The release actuator and tightening actuator are positioned on an exterior of the prosthetic socket. Actuating the release actuator causes the coupling mechanism to transition from the first position to the second position. Actuating the tightening actuator causes the motor to rotate the spool in the first direction to wind the tether around the spool.

18 Claims, 6 Drawing Sheets

(56)                References Cited

U.S. PATENT DOCUMENTS

| 9,248,040 | B2 * | 2/2016 | Soderberg | A41F 1/00 |
| 2017/0151072 | A1 * | 6/2017 | Mahon | A61F 2/78 |
| 2017/0304086 | A1 * | 10/2017 | Kuiken | A61F 2/54 |
| 2020/0368041 | A1 | 11/2020 | Beerens | |

OTHER PUBLICATIONS

Legro et al., "Issue of importance reported by persons with lower limb amputations and prostheses", J. Rehabil Res Dev 1999;36:155-63.

Sanders et al., "How do sock ply changes affect residual limb fluid volume in people with trans-tibial amputation?", J. Rehabil Res Dev 2012; 49:241-56.

Board et al., "A comparison of trans-tibial amputee suction and vacuum socket conditions", Prosthet Orthot Int 2001;25:202-9.

Klute et al., "Vacuum-Assisted Socket Suspension Compared with Pin Suspension for Lower Extremity Amputees: Effect on Fit, Activity, and Limb Volume", Arch Phys Med Rehabil 2011;92:1570-5.

Gerschutz et al., "Dynamic Effectiveness evaluation of Elevated Vacuum Suspension", J Prosthet Orthot 2015;27:161-5.

Wemke et al., "Progress Toward Optimizing Prosthetic Socket Fit and Suspension Using Elevated Vacuum to Promote Residual Limb Health", Adv Wound Care 2017;6:233-9.

Traballesi et al., "Residual limb wounds or ulcers heal in trasntibial amputees using an active suction socket system. A randomized controlled study", Eur J Phys Rehab Med 2012;8:613-23.

Gholizadeh et al., "The evidence-base for elevated vacuum in lower limb prosthetics: literature review and professional feedback", Clin Biomech 2016;37:108-16.

Sanders et al., "Does temporary socket removal affect residual limb fluid volume of trans-tibial amputees?", Prosteht Orthot Int 2016;40(3):320-28.

Youngblood et al., "Effects of activity intensity, time, and intermittent doffing on daily limb fluid volume change in people with transtibial amutation", Prosthet Orthot Int 2019;43(1):28-38.

McLean et al., "Does augmenting panel release with pin release facilitate limb fluid volume recovery in transtibial prosthesis users?", PMR 2019.

Sanders et al., "Preliminary evaluation of a novel bladder-liner for facilitating residual-limb fluid volume recovery without doffing", J Rehabil Res Dev 2016;53(6):1107-20.

Gurrey et al., "Socket release/relock: An innovative mechanism to maintain residual limb volume", Med Eng and Physics 2021;90:100-106.

* cited by examiner

PROSTHETIC SOCKET RELEASE/RELOCK SYSTEM

CROSS-REFERENCE TO RELATED APPLICATIONS

This application claims priority to U.S. Provisional Patent Application No. 63/316,309, filed Mar. 3, 2022, the contents of which are hereby incorporated by reference in their entirety.

STATEMENT REGARDING FEDERAL FUNDING

This invention was made with government support Grant No. W81XWH-18-1-0595, awarded by the Department of Defense. The government has certain rights in the invention.

BACKGROUND

Unless otherwise indicated herein, the materials described in this section are not prior art to the claims in this application and are not admitted to be prior art by inclusion in this section.

Prosthesis users report socket fit is the single-most important issue related to use of their prosthesis. One of the most common causes of prosthetic socket fit problems in people with limb amputation is residual limb volume loss. The traditional management strategy is to add prosthetic socks to reduce socket size and accommodate the smaller residual limb. But reducing socket size further reduces limb fluid volume and may accentuate limb atrophy, necessitating socket replacement.

An alternative accommodation strategy to manage socket size is for prosthesis users to manage their limb volume. Elevated vacuum (EV) systems do that by drawing soft tissues outward during ambulation using a mechanical or electric pump to apply vacuum pressure between the liner and socket. EV has been suggested an effective suspension method and has been shown to reduce vertical displacement during ambulation. However, EV has drawbacks, the most common of which is its fault intolerance to air leaks. EV's continual maintenance need requires a knowledgeable and often technically savvy user. EV systems may be replaced after a short time because of user frustration with inconsistent performance.

An alternative means to management of limb volume loss is to periodically doff the socket to allow for limb volume recovery. In transtibial prosthesis users with pin lock suspension, doffing the socket during 20 to 30-minute rest periods after activity induced significantly greater limb fluid volume during subsequent ambulation than not doffing. However, if the socket was enlarged but the pin was not released then fluid volume recovery and retention were reduced. These results suggest that pin release is a key aspect of partial doffing as an effective accommodation strategy. Partial doffing with pin release can be challenging to perform in user free-living environments, particularly for people who are active and do not have time to repeatedly remove clothing to partially doff their socket during the day.

Accordingly, a mechanism to easily partially doff and re-don a transtibial prosthesis may be desirable.

SUMMARY

The present disclosure provides a device to easily partially doff and re-don a transtibial prosthesis with pin lock suspension. The device tracks the release and tightening of the locking pin, creating a record of socket adjustment that may be useful towards patient care.

In particular, in a first aspect, the present disclosure provides device configured to be positioned within a prosthetic socket. The device includes a tether having a first end and a second end opposite the first end. The first end of the tether is configured to be coupled to a prosthetic liner. The device also includes a spool fixed with respect to the prosthetic socket. The second end of the tether is coupled to the spool. The device also includes a motor fixed with respect to the prosthetic socket, and a battery configured to provide power to the motor. The device also includes a coupling mechanism configured to transition from a first position in which the spool is only able to rotate in a first direction to a second position in which the spool is able to rotate in the first direction and a second direction. The device also includes a release actuator positioned on an exterior of the prosthetic socket. Actuation of the release actuator causes the coupling mechanism to transition from the first position to the second position. The device also includes a tightening actuator positioned on the exterior of the prosthetic socket. Actuation of the tightening actuator causes the motor to rotate the spool in the first direction to wind the tether around the spool to thereby reduce a distance between the first end of the tether and the spool.

These as well as other aspects, advantages, and alternatives, will become apparent to those of ordinary skill in the art by reading the following detailed description, with reference where appropriate to the accompanying drawings.

DETAILED DESCRIPTION

Figure 1:
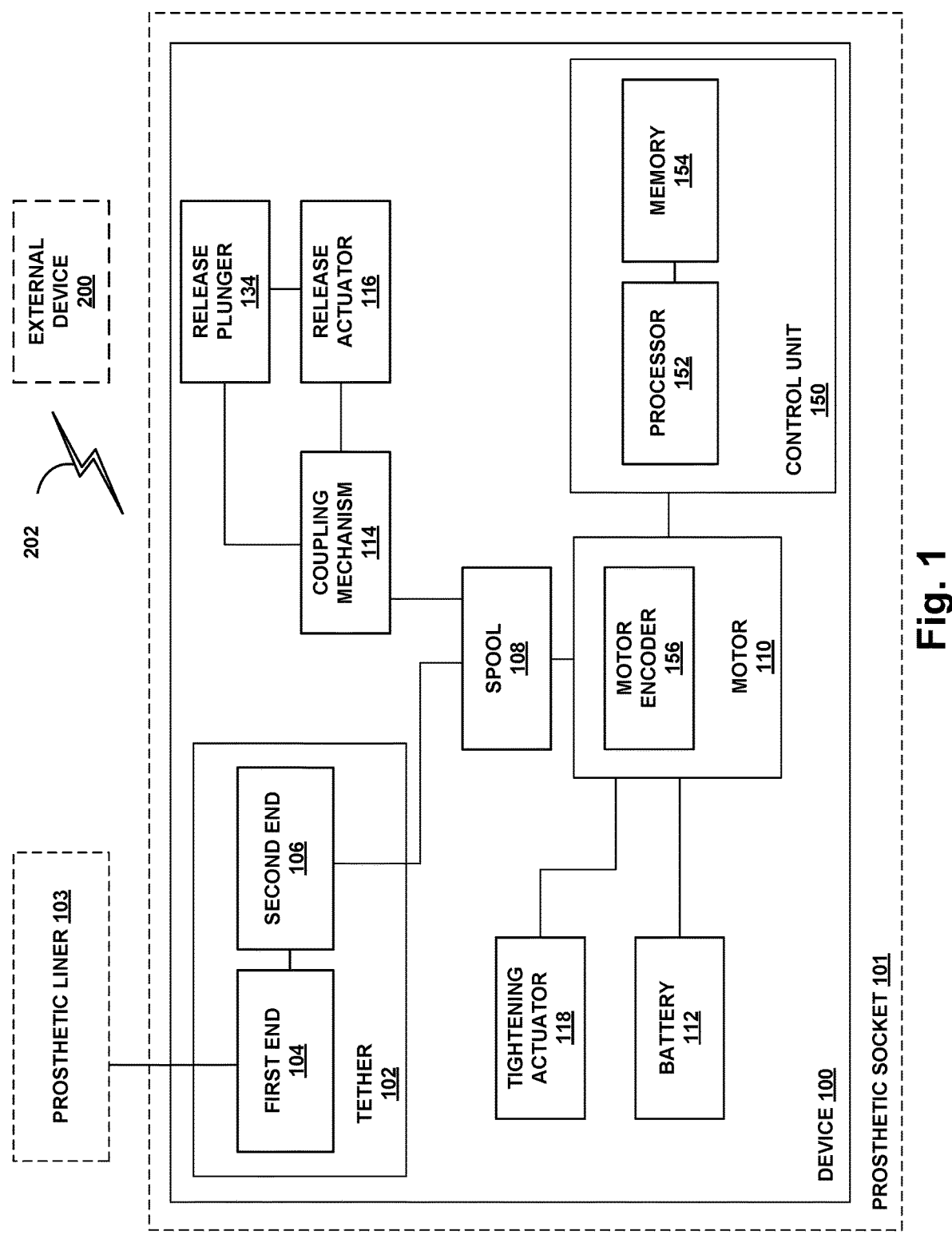
FIG. 1 illustrates a simplified block diagram containing an overview of the components of a device, according to an example embodiment.

Example methods and systems are described herein. It should be understood that the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The example embodiments described herein are not meant to be limiting. It will be readily understood that the aspects of the present disclosure, as generally described herein, and illustrated in the Figures, can be arranged, substituted, combined, separated, and designed in a wide variety of different configurations, all of which are explicitly contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an example embodiment may include elements that are not illustrated in the Figures.

As used herein, "coupled" means associated directly as well as indirectly. For example, a member A may be directly associated with a member B, or may be indirectly associated therewith, e.g., via another member C. It will be understood that not all relationships among the various disclosed elements are necessarily represented.

Unless otherwise indicated, the terms "first," "second," etc. are used herein merely as labels, and are not intended to impose ordinal, positional, or hierarchical requirements on the items to which these terms refer. Reference to, e.g., a "first" item does not require or preclude the existence of, e.g., a "second" or higher-numbered item. Moreover, reference to, e.g., a "second" item does not require or preclude the existence of, e.g., a "first" or lower-numbered item, and/or, e.g., a "third" or higher-numbered item.

Reference herein to "one embodiment" or "one example" means that one or more feature, structure, or characteristic described in connection with the example is included in at least one implementation. The phrases "one embodiment" or "one example" in various places in the specification may or may not be referring to the same example.

As used herein, a system, apparatus, device, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

As used herein, with respect to measurements, "about" means +/−5%.

As used herein, with respect to measurements, "substantially" means+/−10%.

The present disclosure provides a device for releasing prosthetic socket pressures during sitting (partial doffing)

may facilitate recovery and retention of limb fluid volume. The device described herein allows for easy locking pin and socket panel release during sitting and quick relock upon standing. A motor-driven release/relock system housed within the prosthetic socket adjusts locking pin tether length. The user operates the release/relock system using buttons on the prosthetic socket. Pin tether length adjustments are recorded on board for later analysis.

In particular, with reference to the Figures, the present disclosure provides a device 100 configured to be positioned within a prosthetic socket 101. The device 100 includes a tether 102 having a first end 104 and a second end 106 opposite the first end 104. The first end 104 of the tether 102 is configured to be coupled to a prosthetic liner 103. The device 100 further includes a spool 108 fixed with respect to the prosthetic socket 101. The second end 106 of the tether is coupled to the spool 108. The device 100 further includes a motor 110 fixed with respect to the prosthetic socket 101, and a battery 112 configured to provide power to the motor 110. The battery 112 may be rechargeable and may be configured to power the device 100 for a minimum of twelve hours, and preferably for at least one week. In one example, the device 100 may include a battery hatch and the battery 112 can be removed for charging. In another example, the device 100 may include a charging port such that the battery 112 can be kept in the device 100 while being charged.

The device 100 further includes a coupling mechanism 114 configured to transition from a first position in which the spool 108 is only able to rotate in a first direction to a second position in which the spool 108 is able to rotate in the first direction and a second direction. The device 100 also includes a release actuator 116 positioned on an exterior of the prosthetic socket 101. Actuation of the release actuator 116 causes the coupling mechanism 114 to transition from the first position to the second position. The release actuator 116 may comprise a button, a lever, or a switch, as non-limiting examples. The device 100 further includes a tightening actuator 118 positioned on the exterior of the prosthetic socket 101. Actuation of the tightening actuator 118 causes the motor 110 to rotate the spool 108 in the first direction to wind the tether 102 around the spool 108 to thereby reduce a distance between the first end 104 of the tether 102 and the spool 108. The tightening actuator 118 may comprise a button, a lever, or a switch, as non-limiting examples.

Figure 2B:
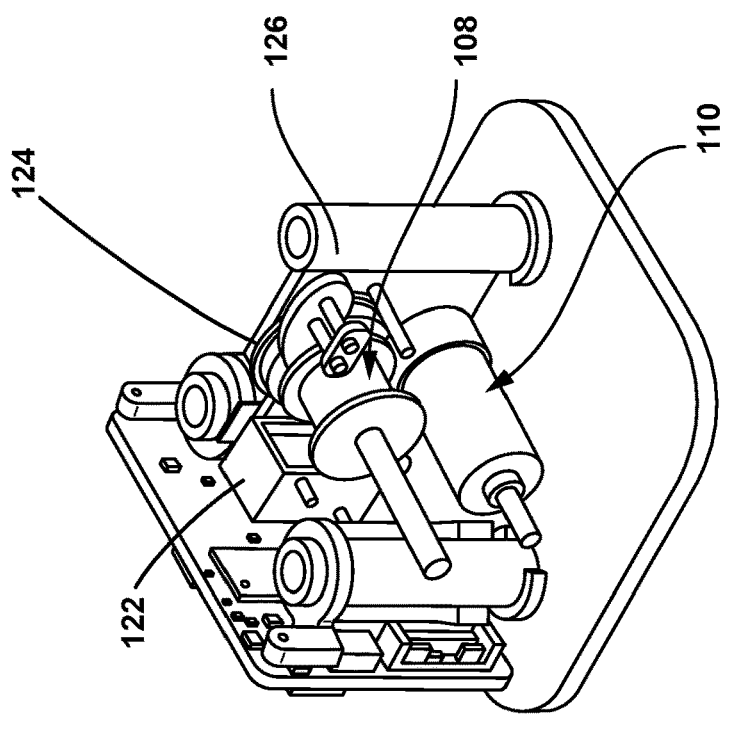
FIG. 2B illustrates a cut-away perspective view of the device of FIG. 2A, according to an example embodiment
Figure 2A:
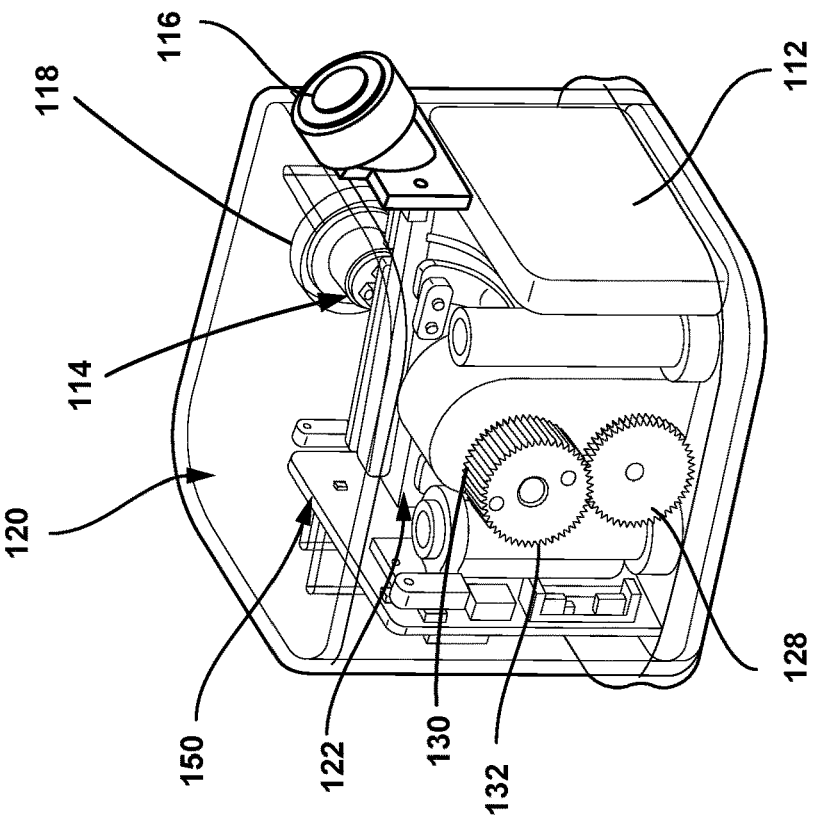
FIG. 2A illustrates a perspective view of some of the components of the device of FIG. 1, according to an example embodiment.

In one example, as shown in FIG. 2A, the device 100 further includes a housing 120 positioned at least partially surrounding the spool 108, the motor 110, the battery 112, and the coupling mechanism 114. In such an example, the first end of the tether 102 extends out from a top surface of the housing 120 so that it can be coupled to the prosthetic liner 103. In one example, the housing 120 is formed integral to the prosthetic socket 101 during fabrication. In another example, the housing 120 is removably coupled to the prosthetic socket 101. In another example, as shown in FIG. 2A, the device 100 includes a first gear 128 coupled to the motor 110, and a second gear 130 coupled to the spool 108. In such an example, the second gear 130 interacts with the first gear 128 to translate rotation of the motor 110 to the spool 108.

In one example, actuation of the tightening actuator 118 causes the coupling mechanism 114 to transition from the second position to the first position. When the coupling mechanism is in the first position, a rotation of the motor 110 translates to a rotation of the spool 108 in the first direction to wind the tether 102 around the spool 108 to thereby reduce the distance between the first end 104 of the tether 102 and the spool 108. An example tightening actuator 118 is shown in FIG. 4A.

Figures 3A, 3B, 3C:
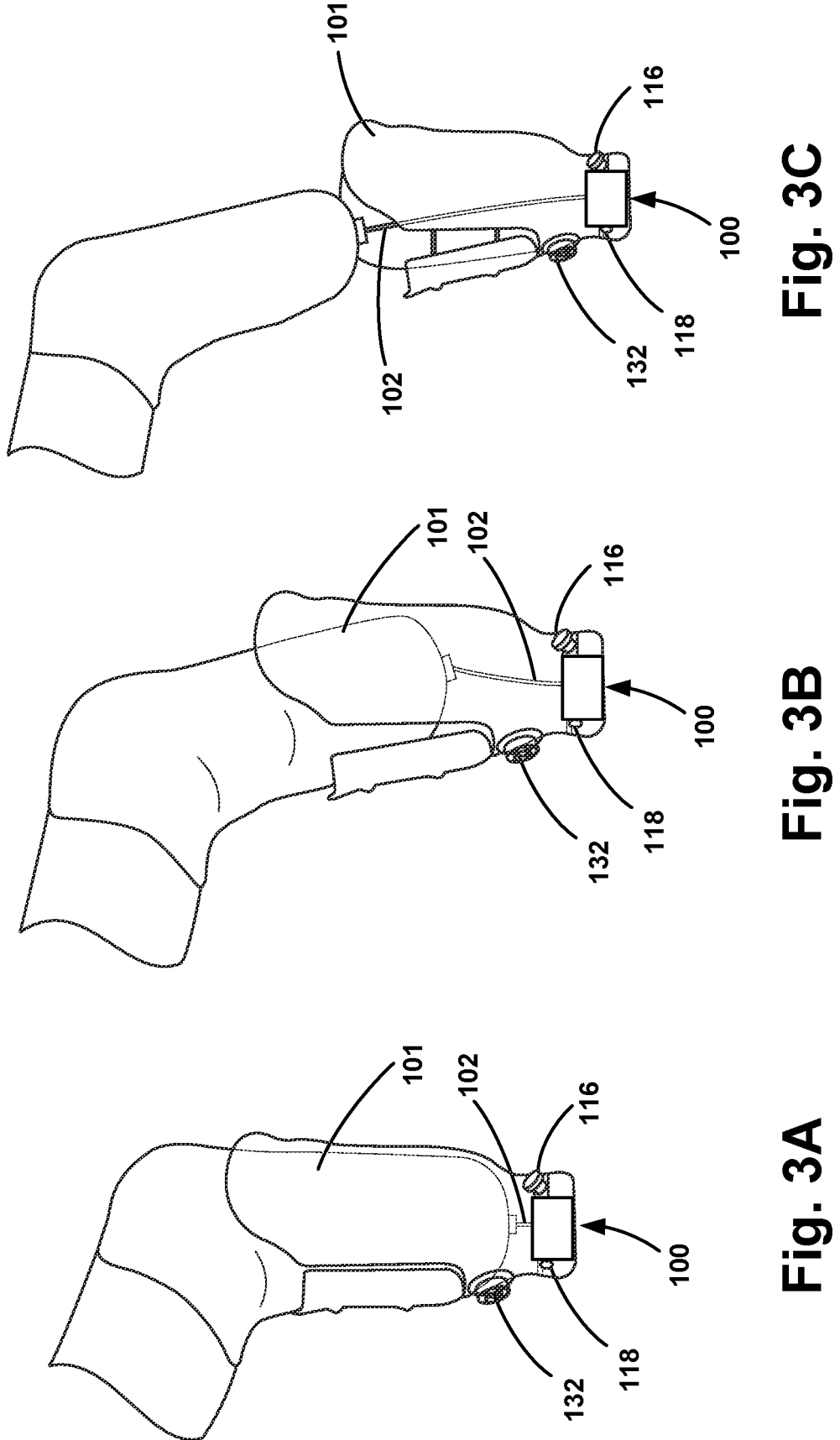
FIG. 3A illustrates the device of FIG. 1 in a fully-donned position, according to an example embodiment.
FIG. 3B illustrates the device of FIG. 1 in a partially-doffed position, according to an example embodiment.
FIG. 3C illustrates the device of FIG. 1 in a fully-doffed position, according to an example embodiment.
Figures 4A, 4B, 4C:
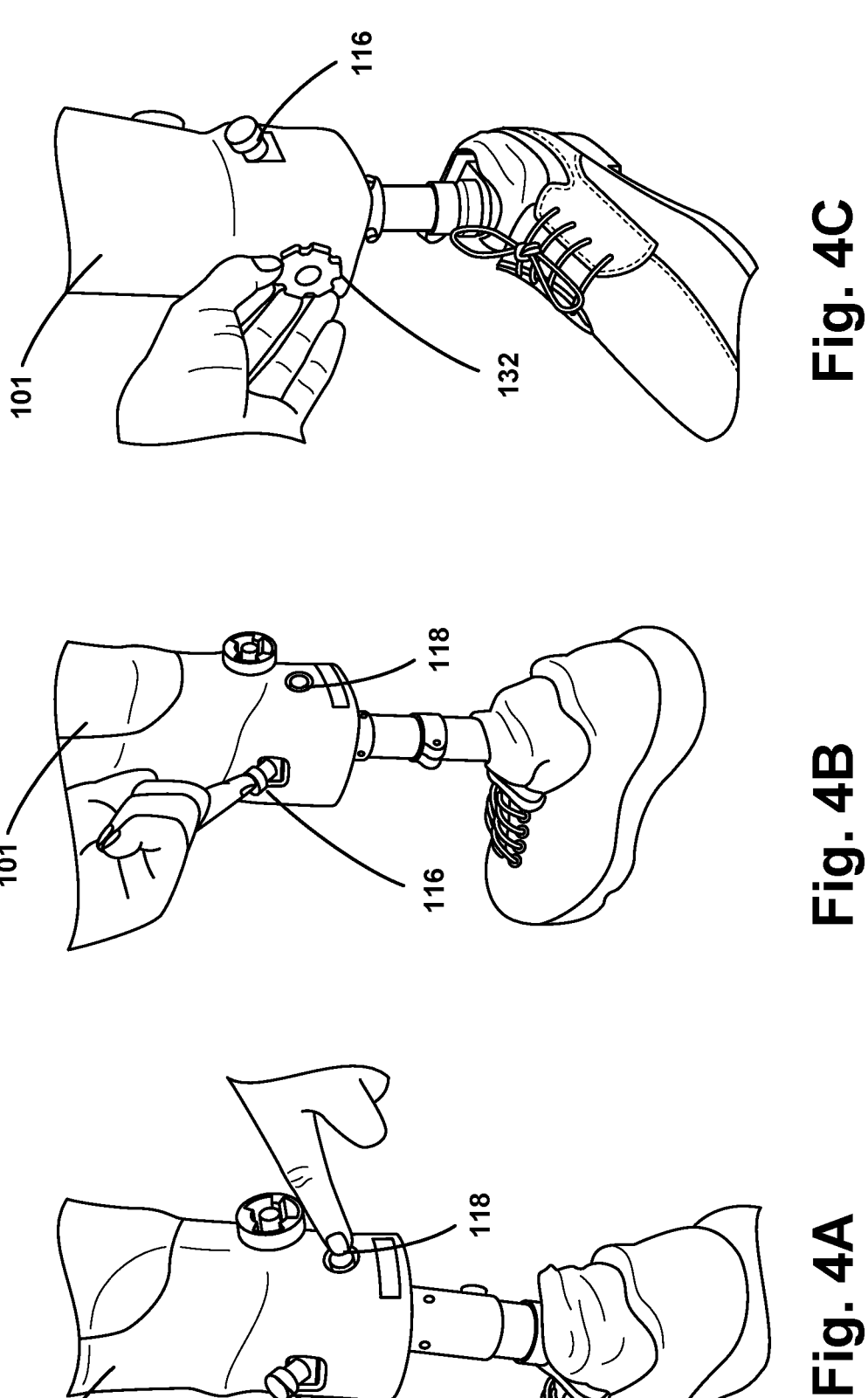
FIG. 4A illustrates a user actuating the tightening actuator of the device of FIG. 1, according to an example embodiment.
FIG. 4B illustrates a user actuating the release actuator of the device of FIG. 1, according to an example embodiment.
FIG. 4C illustrates a user actuating the knob of the device of FIG. 1, according to an example embodiment.

In one example, the release actuator 116 comprises a button, as shown in FIG. 4B. In one such example, pressing the button a first time causes the coupling mechanism 114 to transition from the first position to the second position to thereby enable a user to increase the distance between the first end 104 of the tether 102 and the spool 108 to a first distance to thereby partially doff the prosthetic socket 101. Such a transition can be seen from the fully-donned position shown in FIG. 3A to the partially-doffed position shown in FIG. 3B. In one example, the coupling mechanism 114 automatically transitions from the second position to the first position once the first end 104 of the tether 102 and the spool 108 are separated by the first distance. By transitioning back to the first position, the coupling mechanism 114 temporarily locks the distance between the first end 104 of the tether 102 and the spool 108 at the first distance. In one example, the first distance ranges from about 3 cm to about 10 cm, and preferably is about 5 cm.

In one example, pressing the button of the release actuator 116 a second time when the first end 104 of the tether 102 and the spool 108 are separated by the first distance causes the coupling mechanism 114 to transition from the first position to the second position to thereby enable a user to increase the distance between the first end 104 of the tether 102 and the spool 108 from the first distance to a second distance to thereby fully doff the prosthetic socket 101. In one example, the second distance ranges from about 20 cm to about 50 cm, and preferably is about 30 cm. Such a transition can be seen from the partially-doffed position shown in FIG. 3B to the fully-doffed position shown in FIG. 3C.

In another example, pressing the button of the release actuator 116 for a first length of time causes the coupling mechanism 114 to transition from the first position to the second position to thereby enable a user to increase the distance between the first end 104 of the tether 102 and the spool 108 1082 to a first distance to thereby partially doff the prosthetic socket 101. The coupling mechanism 114 transitions from the second position to the first position once the first end 104 of the tether 102 and the spool 108 are separated by the first distance. Pressing the button for a second length of time that is greater than the first length of time causes the coupling mechanism 114 to transition from the first position to the second position to thereby enable a user to increase the distance between the first end 104 of the tether 102 and the spool 108 to a second distance that is greater than the first distance to thereby fully doff the prosthetic socket 101. As described above, in one example the first distance ranges from about 3 cm to about 10 cm, and preferably is about 5 cm, and the second distance ranges from about 20 cm to about 50 cm, and preferably is about 30 cm.

In one example, the device 100 includes a solenoid 122 coupled to the coupling mechanism 114. Actuation of the solenoid 122 causes the coupling mechanism 114 to transition from the first position to the second position. In one example, the coupling mechanism 114 comprises a ratchet 124 and a pawl mechanism 126. In such an example, the ratchet 124 is fixed with respect to the spool 108, and the pawl mechanism 126 is configured to transition from the first position to the second position. When the pawl mechanism 126 is in the first position, the pawl mechanism 126 engages with the ratchet 124 such that the spool 108 is only able to rotate in the first direction.

When the pawl mechanism 126 transitions to the second position, the pawl mechanism 126 disengages from the ratchet 124 such that the spool 108 is able to rotate in the first direction and the second direction opposite the first direction. In one example, the pawl mechanism 126 is biased to the first position (e.g., via a spring or the mechanism), and the solenoid 122 is used to transition the pawl mechanism 126 from the first position to the second position. When the solenoid 122 is deactivated, the pawl mechanism 126 automatically returns to the first position.

In one example, as shown in FIG. 4C, the device 100 further includes a knob 132 positioned on the exterior of the prosthetic socket 101. The knob 132 is coupled to the spool 108 such that a rotation of the knob 132 in the first direction causes the spool 108 to rotate in the first direction to wind the tether 102 around the spool 108 to thereby reduce the distance between the first end 104 of the tether 102 and the spool 108. Such a knob 132 provides a manual option for tightening the prosthesis in case of emergency, power failure, or malfunction. Referring now to FIG. 1, a push and hold of the release actuator 116 beyond the pressure required to electronically activate the release actuator 116 allows the user to doff the prosthesis even if there is no power by actuating a release plunger 134.

Figure 5B:
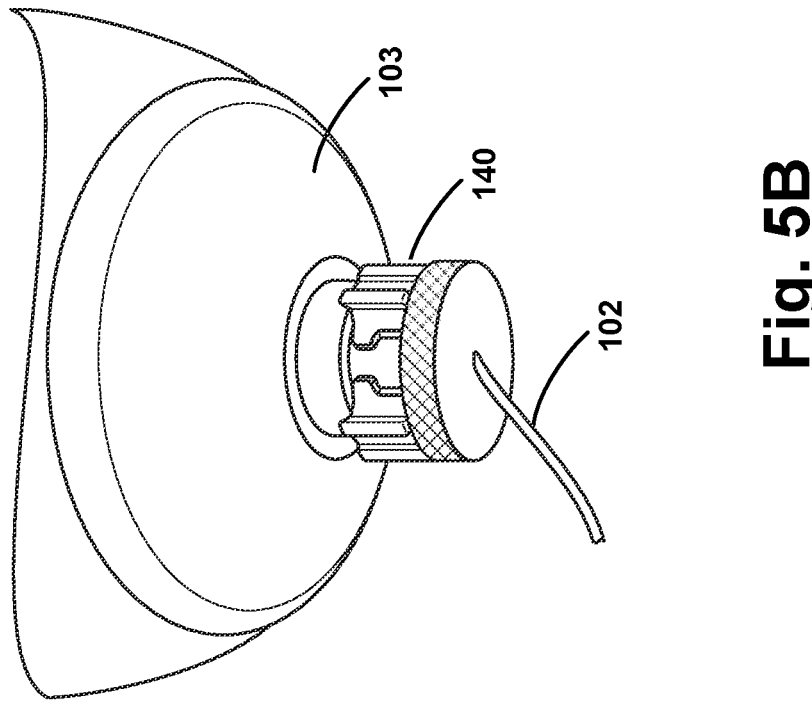
FIG. 5B illustrates the release mechanism of FIG. 5A coupled to a pin of the prosthetic liner, according to an example embodiment.
Figure 5A:
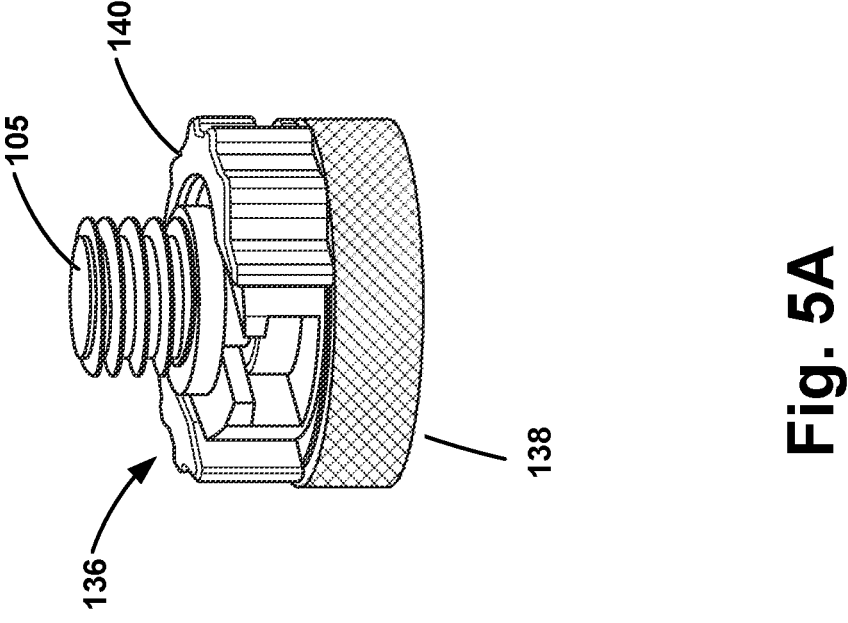
FIG. 5A illustrates a perspective view of an example release mechanism of the device of FIG. 1, according to an example embodiment.

In one example, as shown in FIGS. 5A-5B, the device 100 includes a release mechanism 136 coupled to the first end 104 of the tether 102. The release mechanism 136 is configured to be removably coupled to a pin 105 of the prosthetic liner 103. In one example, the release mechanism 136 includes an opening 138 configured to receive the pin 105 of the prosthetic liner 103, a rotatable component 140 configured to transition from a first position in which the opening 138 is uncovered by the rotatable component 140 to a second position in which the opening 138 is covered by the rotatable component 140.

In one example, as shown in FIG. 1, the device 100 further includes a control unit 150 in communication with the motor 110. The control unit 150 can be any type of controller including, but not limited to, a microprocessor, a microcontroller, a digital signal processor, or any combination thereof. The control unit 150 includes a processor 152 and on-board data storage, such as memory 154 coupled to the processor 152. The memory 154 may store software that can be accessed and executed by the processor 152, for example. The memory 154 can include any type of memory now known or later developed including but not limited to volatile memory (such as RAM), non-volatile memory (such as ROM, flash memory, etc.) or any combination thereof. The control unit 150 may include program instructions that are stored in the memory 154 (and/or possibly in another data-storage medium) and executable by the processor 152 to facilitate the various functions described herein. Although various components of the device 100 are shown as distributed components, it should be understood that any of such components may be physically integrated and/or distributed according to the desired configuration of the device 100.

In one example, the control unit 150 is configured to (i) determine, based on a motor encoder 156 of the motor 110, the distance between the first end 104 of the tether 102 and the spool 108, and (ii) activate the coupling mechanism 114 based on the determined distance.

In another example, the control unit 150 is configured to (i) determine a current of the motor 110, and (ii) stop the motor 110 when the current exceeds a threshold. The current exceeding the threshold indicates that the tether 102 is sufficiently taught and the user's residual limb and liner are positioned properly within the prosthetic socket 101.

In another example, the control unit 150 is configured to (i) record a number of times the release actuator 116 is actuated over a given time period, and (ii) transmit a message indicating the number of times the release actuator 116 is actuated over the given time period. Such a message may provide information to a medical professional on the use of the device 100. The medical professional can use this information to instruct the user or otherwise improve use of the device 100.

In one example, the device 100 communicates with an external device 200 using a communication link 202, such as a wired or wireless connection. The external device 200 may be any type of device that can receive data and display information corresponding to or associated with the data. For example, the external device 200 may be a mobile phone, a tablet, or a personal computer as examples. The device 100 and the external device 200 may contain hardware to enable the communication link 202, such as processors, transmitters, receivers, antennas, etc.

In FIG. 1, the communication link 202 is illustrated as a wireless connection; however, wired connections may also be used. For example, the communication link 202 may be a wired link via a serial bus such as a universal serial bus or a parallel bus. A wired connection may be a proprietary connection as well. The communication link 202 may also be a wireless connection using, e.g., radio technology (including, for example, Bluetooth® technologies), communication protocols described in IEEE 802.11 (including any IEEE 802.11 revisions), Cellular technology (such as GSM, CDMA, UMTS, EV-DO, WiMAX, or LTE), or short-range wireless protocols (such as Zigbee® technology), among other possibilities.

Figure 6:
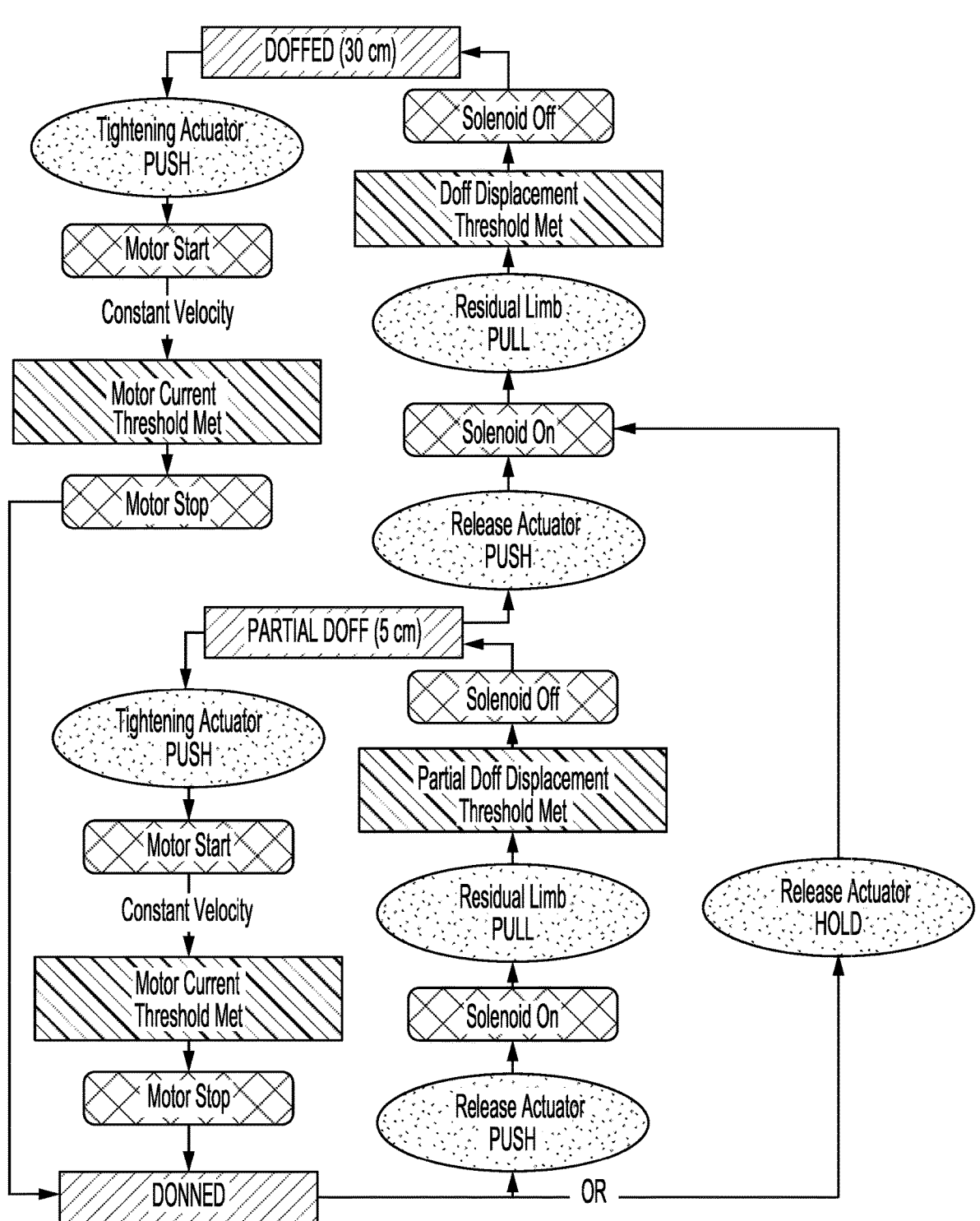
FIG. 6 illustrates a flowchart of a method of using the device of FIG. 1, according to an example embodiment.

FIG. 6 illustrates a flowchart of a method of using the device 100 described above in relation to FIGS. 1-5B. In particular, in use the user dons an elastomeric liner with the release mechanism 136 tethered to the device 100. The tether 102 passes through the hole in the distal socket (tether length up to 45 cm, typically 30 cm is used). While sitting or standing, the user dons the prosthetic socket 101. The user pushes the tightening actuator 118 on the posterior aspect of the prosthetic socket 101 once to activate the motor 110. The motor 110 winds the tether 102 around the spool 108, drawing the user's residual limb and liner into the prosthetic socket 101.

The device 100 monitors motor current to determine when a threshold (high) current is met, indicating that the tether 102 is sufficiently taught to stop the motor 110. After transitioning from sitting to standing (if initially sitting), the user may press the tightening actuator 118 again if there is slack in the tether 102, e.g. from the liner umbrella compressing upon standing.

To partially doff the prosthetic socket 101, the user pushes the release actuator 116 once.

This action transitions the coupling mechanism 114 from a first position in which the spool 108 is only able to rotate in a first direction to a second position in which the spool 108 is able to rotate in the first direction and a second direction (e.g., the device 100 powers on the solenoid 122 that pushes the pawl mechanism 126 off the ratchet 124). The device 100 will now allow the user to pull the residual limb out of the prosthetic socket 101, back driving the motor 110. When the partial doff threshold (e.g., a distance specified in the control unit 150) is met, the coupling mechanism 114 transitions from the second position to the first position (e.g., powers off the solenoid 122 so that the pawl mechanism 126 reengages with the ratchet 124).

To fully release the tether 102 and doff the socket, the user pushes the release actuator 116 again. If the device 100 is previously in partial doff mode, then a single push of the release actuator 116 will fully release the tether 102. Otherwise, the user holds the release actuator 116 continuously to fully release the tether 102 to allow the user to pull the limb out of the prosthetic socket 101. In one example, similar to the partial doff embodiment described above, when the full doff threshold (e.g., a distance specified in the control unit 150) is met, the coupling mechanism 114 transitions from the second position to the first position (e.g., powers off the solenoid 122 so that the pawl mechanism 126 reengages with the ratchet 124). In another example, the control unit 150 utilizes a timeout instead of a displacement threshold for transitioning the coupling mechanism 114 from the second position to the first position. For example, the timeout may be between about 5 seconds and about 15 seconds, and preferably about 8 seconds. In such an example, after the timeout period the coupling mechanism 114 automatically transitions from the second position to the first position (e.g., powers off the solenoid 122 so that the pawl mechanism 126 reengages with the ratchet 124).

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

Since many modifications, variations, and changes in detail can be made to the described example, it is intended that all matters in the preceding description and shown in the accompanying figures be interpreted as illustrative and not in a limiting sense. Further, it is intended to be understood that the following clauses (and any combination of the clauses) further describe aspects of the present description.

We claim:

1. A device configured to be positioned within a prosthetic socket, the device comprising:
    a tether having a first end and a second end opposite the first end, wherein the first end of the tether is configured to be coupled to a prosthetic liner;
    a spool fixed with respect to the prosthetic socket, wherein the second end of the tether is coupled to the spool;
    a motor fixed with respect to the prosthetic socket, the motor comprising a motor encoder;
    a battery configured to provide power to the motor;
    a coupling mechanism configured to transition from a first position in which the spool is only able to rotate in a first direction to a second position in which the spool is able to rotate in the first direction and a second direction;

a release actuator positioned on an exterior of the prosthetic socket, wherein actuation of the release actuator causes the coupling mechanism to transition from the first position to the second position;

a tightening actuator positioned on the exterior of the prosthetic socket, wherein actuation of the tightening actuator causes the motor to rotate the spool in the first direction to wind the tether around the spool to thereby reduce a distance between the first end of the tether and the spool; and a control unit in communication with the motor, wherein the control unit is configured to:

determine, based on the motor encoder, the distance between the first end of the tether and the spool; and activate the coupling mechanism based on the determined distance.

2. The device of claim 1, further comprising a housing positioned at least partially surrounding the spool, the motor, the battery, and the coupling mechanism.

3. The device of claim 2, wherein the housing is formed integral to the prosthetic socket during fabrication.

4. The device of claim 1, wherein the device is removably coupled to the prosthetic socket.

5. The device of claim 1, wherein actuation of the tightening actuator causes the coupling mechanism to transition from the second position to the first position.

6. The device of claim 1, wherein the release actuator comprises a button, and wherein pressing the button a first time causes the coupling mechanism to transition from the first position to the second position to thereby enable a user to increase the distance between the first end of the tether and the spool to a first distance to thereby partially doff the prosthetic socket, and wherein the coupling mechanism transitions from the second position to the first position once the first end of the tether and the spool are separated by the first distance.

7. The device of claim 6, wherein the first distance ranges from about 3 cm to about 10 cm.

8. The device of claim 6, wherein pressing the button a second time when the first end of the tether and the spool are separated by the first distance causes the coupling mechanism to transition from the first position to the second position to thereby enable a user to increase the distance between the first end of the tether and the spool from the first distance to a second distance to thereby fully doff the prosthetic socket.

9. The device of claim 8, wherein the second distance ranges from about 20 cm to about 50 cm.

10. The device of claim 1, wherein the release actuator comprises a button, wherein pressing the button for a first length of time causes the coupling mechanism to transition from the first position to the second position to thereby enable a user to increase the distance between the first end of the tether and the spool to a first distance to thereby partially doff the prosthetic socket, wherein the coupling mechanism transitions from the second position to the first position once the first end of the tether and the spool are separated by the first distance, and wherein pressing the button for a second length of time that is greater than the first length of time causes the coupling mechanism to transition from the first position to the second position to thereby enable a user to increase the distance between the first end of the tether and the spool to a second distance that is greater than the first distance to thereby fully doff the prosthetic socket.

11. The device of claim 10, wherein the first distance ranges from about 3 cm to about 10 cm, and wherein the second distance ranges from about 20 cm to about 50 cm.

12. The device of claim 1, further comprising:

a solenoid coupled to the coupling mechanism, wherein actuation of the solenoid causes the coupling mechanism to transition from the first position to the second position.

13. The device of claim 1, further comprising:

a first gear coupled to the motor; and a second gear coupled to the spool, wherein the second gear interacts with the first gear to translate rotation of the motor to the spool.

14. The device of claim 1, further comprising:

a knob positioned on the exterior of the prosthetic socket, wherein the knob is coupled to the spool such that a rotation of the knob in the first direction causes the spool to rotate in the first direction to wind the tether around the spool to thereby reduce the distance between the first end of the tether and the spool.

15. The device of claim 1, wherein the coupling mechanism comprises a ratchet and a pawl mechanism, wherein the ratchet is fixed with respect to the spool, and wherein the pawl mechanism is configured to transition from the first position to the second position.

16. The device of claim 1, further comprising:

a release mechanism coupled to the first end of the tether, wherein the release mechanism is configured to be removably coupled to a pin of the prosthetic liner.

17. The device of claim 16, wherein the release mechanism comprises:

an opening configured to receive the pin of the prosthetic liner; and a rotatable component configured to transition from a first position in which the opening is uncovered by the rotatable component to a second position in which the opening is covered by the rotatable component.

18. The device of claim 1, wherein the control unit is configured to:

record a number of times the release actuator is actuated over a given time period; and transmit a message indicating the number of times the release actuator is actuated over the given time period.

* * * * *